(12) United States Patent
Schwab et al.

(10) Patent No.: US 11,779,679 B2
(45) Date of Patent: Oct. 10, 2023

(54) TISSUE-ADHESIVE MATERIAL

(71) Applicant: Polyganics IP B.V., Groningen (NL)

(72) Inventors: Leendert Willem Schwab, Groningen (NL); Konstantin Igorovitch Denisov, Leeuwarden (NL); Martin Franke Tooren, Bedum (NL); Theodorus Petrus Cornelis Van Doormaal, Groningen (NL)

(73) Assignee: Polyganics IP B.V., Groningen (NL)

( * ) Notice: Subject to any disclaimer, the term of this patent is extended or adjusted under 35 U.S.C. 154(b) by 199 days.

(21) Appl. No.: 17/204,093

(22) Filed: Mar. 17, 2021

(65) Prior Publication Data

US 2021/0213158 A1 Jul. 15, 2021

Related U.S. Application Data

(62) Division of application No. 16/089,507, filed as application No. PCT/NL2017/050200 on Mar. 31, 2017, now abandoned.

(30) Foreign Application Priority Data

Mar. 31, 2016 (NL) ...................................... 2016524

(51) Int. Cl.
*A61L 24/00* (2006.01)
*A61L 24/04* (2006.01)

(52) U.S. Cl.
CPC ......... *A61L 24/043* (2013.01); *A61L 24/0015* (2013.01); *A61L 24/0031* (2013.01); *A61L 24/0036* (2013.01); *A61L 24/0042* (2013.01); *A61L 24/0094* (2013.01); *A61L 2430/34* (2013.01)

(58) Field of Classification Search
CPC ............... A61L 24/043; A61L 24/0015; A61L 24/0031; A61L 24/0036; A61L 24/0042; A61L 24/0094; A61L 2430/34
See application file for complete search history.

(56) References Cited

U.S. PATENT DOCUMENTS

| | | | |
|---|---|---|---|
| 2011/0081417 A1 | 4/2011 | Sargeant et al. | |
| 2011/0087272 A1 | 4/2011 | Sargeant et al. | |
| 2015/0290356 A1 | 10/2015 | Behrens et al. | |

FOREIGN PATENT DOCUMENTS

| CN | 101378791 A | | 3/2009 |
|---|---|---|---|
| CN | 102028968 A | | 4/2011 |
| CN | 104414772 A | | 3/2015 |
| EP | 1025870 A1 | | 8/2000 |
| WO | 2006/013337 A2 | | 2/2006 |
| WO | 2006/021054 A1 | * | 3/2006 |
| WO | 2007/088402 A2 | | 8/2007 |

OTHER PUBLICATIONS

Certificate of Analysis, 8arm PEG Succinimidyl Glutarate (hexaglycerol), MW 40000. Signed Feb. 2, 2016. Jenkem Technology PEG Derivatives and Pegylation Services.

* cited by examiner

*Primary Examiner* — Alma Pipic
(74) *Attorney, Agent, or Firm* — Banner & Witcoff, Ltd.

(57) ABSTRACT

The invention is directed to a tissue-adhesive polymer blend comprising a bioresorbable carrier polymer and a bioresorbable synthetic tissue-reactive polymer as well as to a tissue-adhesive device for sealing dura mater comprising said tissue-adhesive polymer blend.

19 Claims, 3 Drawing Sheets

TISSUE-ADHESIVE MATERIAL

RELATED APPLICATIONS

This application is a Divisional application which claims priority to U.S. application Ser. No. 16/089,507, filed on Sep. 28, 2018, which is a National Stage Application under 35 U.S.C. 371 of co-pending PCT application PCT/NL2017/050200 designating the United States and filed Mar. 31, 2017; which claims the benefit of NL application number 2016524 and filed Mar. 31, 2016 each of which are hereby incorporated by reference in their entireties.

The invention is in the field of bioresorbable adhesive materials for medical applications. In particular, the invention is directed to a tissue-adhesive polymer blend and devices comprising such a blend, which are used for sealing dura mater.

Figure 1:
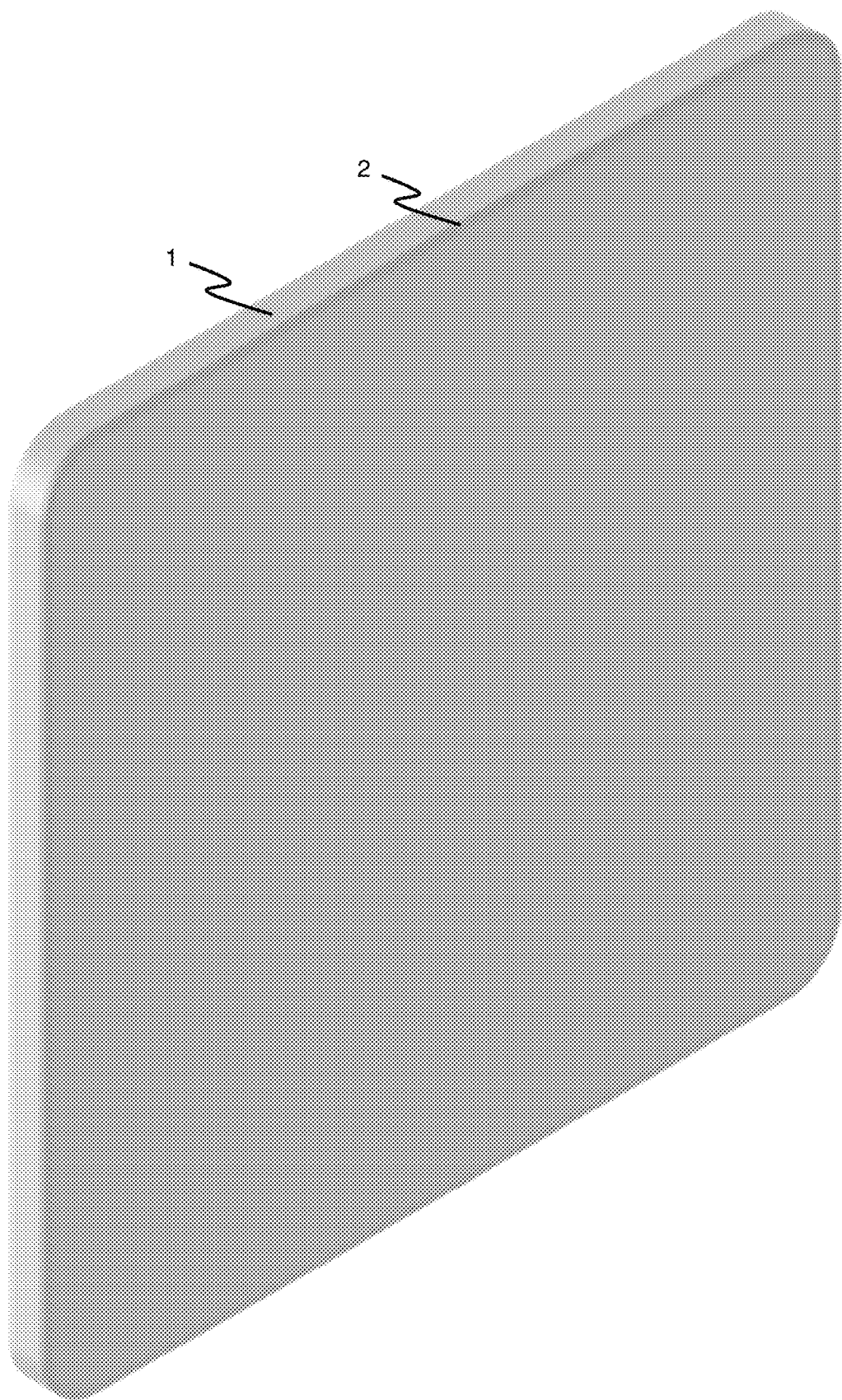
FIG. 1 is an illustration of a tissue-adhesive device for sealing dura mater as disclosed herein.

Tissue-adhesive materials are used in a variety of medical applications. These materials are for instance used to cover or seal wounds to prevent or reduce leakage of bodily fluids. A particular application for tissue-adhesive materials is the sealing of dura mater. Dura mater is the outermost membrane layer that surrounds the brain and spinal cord of the central nervous system. After e.g. trauma or cranial surgery, opened dura mater needs to be sealed to prevent leakage of cerebrospinal fluid. Even when in an operation dura mater is closed by suture, staples and such, cerebrospinal fluid may still leak, in particular through remaining small openings. It is therefore typically required that the dura mater is sealed by a surgical sealant. Preferably, this sealant material is based on a tissue-adhesive material such that no glue or other type of adhesive is required to apply the sealant and seal the dura mater.

It is desired that the tissue-adhesive material is characterized by a number of properties. The tissue-adhesive bioresorbable material should be biocompatible meaning that it is non-toxic and cause minimal inflammatory and/or immune response. It is further preferred that the tissue-adhesiveness does not have irritating effect and/or inhibit the healing process of the tissue. This biocompatibility may inter alia be achieved by a bioresorbable nature of the material. Bioresorbability in this respect means that the material can be broken down by, and be cleared from the body and does not require mechanical removal. The breakdown of the materials typically occurs through hydrolysis or enzymatic cleavage into smaller compounds that may be metabolized or excreted, for instance via the kidneys or liver.

It is further required that the device has a sufficient adhesive strength to dura mater. Additionally, the device is preferably sufficiently burst-resistant, preferably for the entire period that is required for the dura mater to heal and close. Sufficient adhesive strength and burst resistance are prerequisites for appropriate sealing of dura mater. Moreover, it is preferred that the device is applied easily by a surgeon during surgery.

Some known tissue-adhesive dura sealants are based on in situ hydrogel formation (e.g. DuraSeal™). These hydrogel-forming materials are typically based on a two-component system of which the components are separately but simultaneously applied on the tissue to be sealed. The two components then form a hydrogel on the surface of the tissue thereby sealing it. A drawback of such two-component based system is the difficult handling of systems during surgery. Moreover, since the lifetime of the hydrated components is limited, two-component systems typically have to be freshly prepared (hydrated) before use. Additionally, hydrogels such as DuraSeal™ are associated with post-operative swelling with the risk of post-operative compression of e.g. the spinal cord (see e.g. Lee et al., Korean Journal Spine 10 (March 2013) 44-46).

A tissue-adhesive device is disclosed in WO2011/079336 and available under the trade name Hemopatch™. A drawback of this patch is its small adherence strength towards dura mater making it ineffective in sealing dura mater.

WO2009/019516 discloses another tissue-adhesive device available under the trade name TissuePatchDural™. Drawbacks of TissuePatchDural™ are its low adherence strength to dura mater and limited durable burst-resistance meaning that its (dura mater) sealant properties are reduced over time and typically lost within 24 hours. Moreover, the poly(acrylic acid) based polymers from which the patch is made are only limited bioresorbable.

The present inventors have found a polymer blend that can be used for the production of a tissue-adhesive device that accommodates the above properties and at least partially solves the drawbacks of the known tissue-adhesive devices. The present invention thus provides a tissue-adhesive polymer blend comprising a bioresorbable carrier polymer and a bioresorbable synthetic tissue-reactive polymer.

The carrier polymer is present in the blend to provide structural support to the device that comprises the polymer blend. Suitable carrier polymers may be synthetic or biological.

Preferably, a synthetic carrier polymer comprises polyesters, polyethers, polyhydroxyacids, polylactones, polyetheresters, polycarbonates, polydioxanes, polyanhydrides, polyurethanes, polyester(ether)urethanes, polyurethane urea, polyamides, polyesteramides, poly-orthoesters, polyaminoacids, polyphosphonates, polyphosphazenes and combinations thereof. Preferably, the synthetic carrier polymer consists of polyesters and/or polyethers. Preferred polyesters are based on lactide (D and/or L), ε-caprolactone, glycolide and combinations thereof.

Particular good results have been achieved with the synthetic carrier polymer that comprises a poly(DL-lactide-co-ε-caprolactone) copolymer obtainable by the copolymerizaton of DL-lactide and ε-caprolactone, which copolymer preferably has a lactide content of 51-75 mol %, more preferably of 55-70 mol %, most preferably of 62-69 mol %. In a particular embodiment, the polyester such as poly(DL-lactide-co-ε-caprolactone) copolymer, is a block (or segment) of a larger polymer, such as a block in polyurethanes as disclosed in WO99/64491 and WO2004/062704 (which are both incorporated herein in their entirety).

It is preferred that the synthetic carrier polymer is the poly(DL-lactide-co-ε-caprolactone) copolymer. This copolymer is disclosed in e.g. WO2003/066705 (which is incorporated herein in its entirety).

In the embodiment wherein the carrier polymer is biological, the biological carrier polymer typically comprises a polysaccharide that is preferably selected from the group consisting of amylose, amylopectine and/or glycogen. Particular good results have been achieved with amylopectine which is thus preferred for the biological carrier polymer.

Advantageously, the synthetic carrier polymer makes it possible to easily vary the structure of the device (i.e. for instance a foam, gel or sheet may be formed). Moreover the bioresorbability of the synthetic carrier polymer can be modified by variation of the chemical composition.

The tissue-adhesive properties of the polymer blend originate inter alia from the tissue-reactive polymer that comprises a tissue-reactive group. With tissue-reactive functional group is meant any chemical group, functionality or moiety that may react with tissue and form a covalent bond. Cells (and thus the tissue that is formed by cells) typically comprises protein and carbohydrates on the outer surface that may react in a variety of reactions. The present invention is thus based on the idea that the tissue-reactive polymer reacts with the tissue and a covalent bond is formed. For instance, amines of proteins may react with activated ester to form amide bonds or a sulfide may react with another sulfide to form a disulfide bond. It may be appreciated that other bonding types, such as Van-der-Waals interactions, hydrogen bonding, ionic interaction and the like, may also play a role in the overall bonding capacity of the tissue-reactive polymer of the present invention. The specific occurrence and strength of each type of bonding generally depends on the type of tissue, the chemical composition of the tissue-reactive polymer and the structure of the device based thereon.

The tissue-reactive functional group is appropriately stable in an aqueous environment, but at the same time sufficiently reactive with respect to the tissue. Although the tissue-reactive functional group may be sensitive to hydrolysis, appropriately stable means that the group remains stable for a period long enough for the tissue-adhesive polymer to react with the tissue. As such, preferred tissue-reactive polymers in accordance with the present invention comprise a tissue-reactive functional group that is an activated ester, an acid chloride, an anhydride, an aldehyde, p-nitrophenyl carbonate, epoxide, an isocyanate, vinyl sulfone, maleimide, o-pyridyl-disulfide, a thiol or combinations thereof. Activated esters, acid chlorides, anhydrides, aldehydes, vinyl sulfone, maleimide and isocyanates are electrophilic groups that may typically react with an amine or another nucleophile of the tissue. Thiol or o-pyridyl-disulfide may form a disulfide bond with the tissue.

Particularly preferred as the tissue-reactive functional group are activated esters. The activated ester may be a thioester, a perfluoroalkyl ester, a pentafluorophenol ester, a N-hydroxysuccinimide (NHS) ester, derivatives thereof, as well as combinations of these. Particularly good results have been obtained with N-hydroxysuccinimide ester, as this ester is stable enough to allow easy handling but also allows a good tissue-bonding. N-hydroxysuccinimide ester or derivatives thereof is therefore most preferred. Examples of derivatives of NHS ester are N-hydroxysulfosuccinimide and salts thereof.

In a particularly preferred embodiment of the present invention, the tissue-reactive polymer is based on polyethylene glycol, preferably based on a multi-arm polyethylene glycol (PEG), more preferably a 4-arm or an ε-arm polyethylene glycol, most preferably an ε-arm polyethylene glycol.

It was surprisingly found that in case the tissue-reactive polymer is based on a multi-arm polyethylene glycol, the adhesive strengths of the tissue-reactive polymer to tissue, in particular to dura mater, is greatly improved. Such an improved tissue-adhesive strength of multi-arm-PEG-based blends is observed even if the number of tissue-reactive groups per gram of the tissue-adhesive polymer blend is lower compared to tissue-reactive polymer blends that are not based on multi-arm PEG (e.g. linear PEG-based tissue-adhesive polymers). Using a multi-arm PEG based tissue-reactive polymer thus allows the use of less of this polymer in the blend to obtain the same tissue-adhesive strength or the use of a similar amount of this polymer in the blend to obtain a higher tissue-adhesive strength when for instance compared to linear PEG-based tissue-adhesive polymers. There is thus a strong synergistic effect between PEG-based tissue-adhesive polymers and the multiplicity of the arms of such polymers.

A multi-arm PEG is typically based on a core comprising multiple anchoring groups where polyethylene glycol arms or groups can be joined. Since the core is typically relatively small compared to the PEG arms, the multi-arm PEG may typically be regarded as star-shaped. However, the core may also comprise a larger component such as a polymer (e.g. polyethylene glycol) and may thus also be of a considerable length and weight. A typically core for a 4-arm PEG may for instance be based on erythritol or pentaerythritol while a typically core for an 8-arm PEG may for instance be based on hexaglycerol. The distal end of each arm is typically functionalized with a spacer that is functionalized with the tissue-reactive functional group.

The multi-arm PEG may be varied in terms of the composition of the core, arm length, spacer composition, spacer length and composition of the tissue-reactive functional group. The arms in a multi-arm PEG are typically of about the same molecular weight (and thus size).

The tissue-reactive polymer preferably has a molecular weight of 2000 to 100000 g/mol, preferably 10000 to 80000 g/mol, more preferably 20000 to 60000 g/mol, most preferably about 40000 g/mol.

The tissue-reactive polymer is typically a complex compound that requires elaborative synthetic efforts and as such relatively expensive in comparison to the carrier polymer. It is therefore preferred to use the minimal amount of tissue-reactive polymer required for an adequate tissue-adhesiveness of the polymer blend and/or the device thereof. As such, the ratio carrier polymer and tissue-reactive polymer in the material (calculated on the weight) is 1:10 to 10:1.

The more preferred ratio may depend on the application of the blend in the device. For instance, the blend may be used in a single-layered tissue-adhesive devices or in a multi-layered (e.g. bi-layered) device (vide infra). In the case that the tissue-adhesive device is single-layered, the ratio carrier polymer tot adhesive polymer is preferably 1:10, more preferably 1:5, most preferably 1:3. In case the tissue-adhesive device is multi-layered, the ratio carrier polymer to adhesive polymer may be 10:1, more preferably 5:1, most preferably 3:1.

In a preferred embodiment of the present invention, the tissue-adhesive polymer blend further comprises a buffering agent, preferably a buffering agent having a pH of more than 7, more preferably in the range of 8 to 10. It was surprisingly found that the presence of the buffering agent improved the tissue-adhesive properties of the tissue-adhesive polymer blend. Without wishing to be bound by theory, the inventors believe that the buffering agent provides locally a favorable (preferably elevated) pH-value under which the rate of the reaction of the tissue with the tissue-reactive polymer is higher.

The buffering agent is preferably not detrimental to the degradation properties of the polymer blend. In addition, the buffering agent is preferably biocompatible. Accordingly, the buffering agent is preferably selected from the group consisting of phosphates (e.g. $Na_2HPO_4$), carbonates, acetates, citrates, Good's buffers (preferably those applicable in a pH range of more than 7, more preferably more than 8) such as bicine and the like.

In a particular embodiment, additionally to the carrier polymer and the tissue-reactive polymer, a filler polymer may be present. The filler polymer is typically based on polyethylene glycol that is not functionalized with the tissue-reactive functional group. The function of the filler polymer is to provide stiffness to the carrier polymer.

The tissue-adhesive polymer blend in accordance with the present invention may be for use in a method of surgery, in particular in a method of sealing dura mater.

A further aspect of the present invention is directed to a tissue-adhesive device for sealing dura mater comprising the tissue-adhesive polymer blend. The device may have a foam structure, a sheet structure, a gel-like structure or combinations thereof. Particular good results have been obtained with a foam structure, which is therefore preferred.

Figure 2:
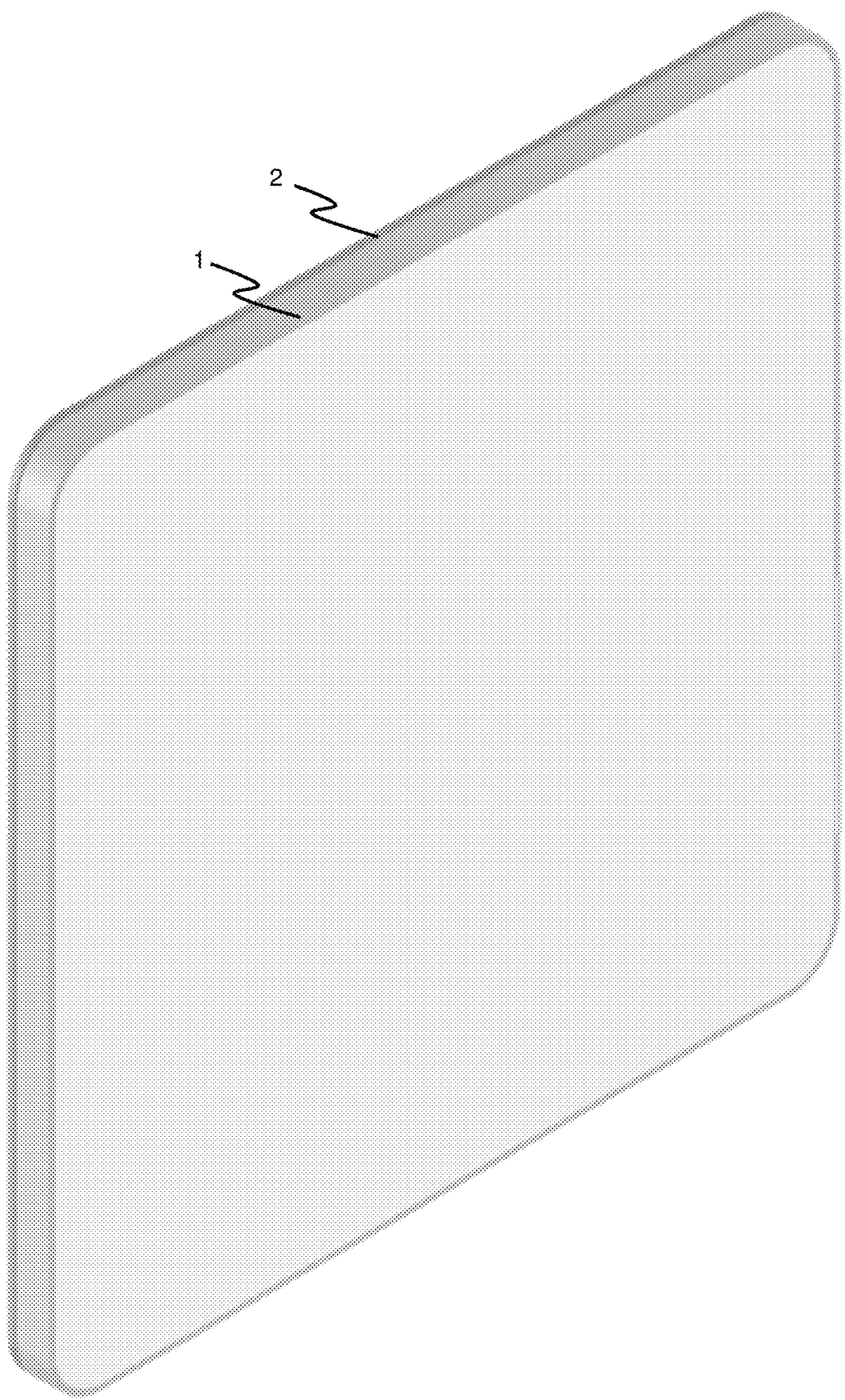
FIG. 2 is an alternative view of the tissue-adhesive device shown in FIG. 1 for sealing dura mater as disclosed herein.

In a preferred embodiment of the device, a illustrated in FIGS. 1 and 2, the device comprises a foam layer (1) of the polymer blend which is are least partially covered by sheet layer (2). It was found that the sheet layer can provide additional resistance towards leakage and burst. It is preferred that the sheet layer is colored differently than the foam layer such that when in use, the tissue-adhesive (foam) layer can more easily be distinguished form the sheet layer.

The sheet layer may for instance comprise a polyester or a polyurethane. Preferably, the sheet layer comprises a polyurethane, more preferably a polyurethane based on diisocyanate linked polyester polymer and diol components as described in WO99/64491. Most preferably, such a polyurethane is based on 50150 D,L-lactide/ε-caprolactone copolyester prepolymer (PP) end-capped with 4-butanediisocyanate and polymerized with a diol based on two 1,4-butane diol components (BDO) which are linked by a 1,4-butanediisocyanate (BDI)—i.e. a polyurethane having a structure of $(BDI-PP-BDI-BDO-BDI-BDO)_n$.

Preferably, the device or the above-described foam layer (1) consist essentially of the tissue-adhesive polymer blend.

Other components such as drugs (e.g. hemostatic, anti-inflammatory agents and the like), may also be present in the device, as long as these components do not undesirably interfere with the adhesive properties of the device.

Typically, the tissue-adhesive device has a multilayered structure comprising at least two layers. A first layer comprises the tissue-adhesive polymer blend and a second layer essentially consisting of the carrier polymer optionally blended with the filler polymer. The first layer will be applied to the dura mater for adhesion and the second layer will mainly provide support. In another embodiment, the concentration of the tissue-reactive polymer varies gradually in the direction perpendicular to the plane of the device that may adhere to the dura mater. In such embodiments, the required amount of tissue-reactive polymer may be limited.

The inventors have found that the device in accordance with the present invention adheres surprisingly well to dura mater and bone tissue. It was furthermore found that adhesion of devices in general, thus including the devices known in the prior part, may vary depending on the type of tissue to adhere to. For instance, a device adhering well to liver tissue may adhere only moderately to dura mater. It was found in fact, that dura mater is particularly difficult to adhere to.

The device in accordance with the present invention preferably has an adhesive strength of more than 1.0 N. The adhesive strength is determined by slicing a piece of dura mater into two slices and adhering the device to both slices such that the slices are joined at their point of slicing to form a bond between the device and the dura mater. By using a universal testing machine, the joined slices are pulled apart at 10 mm/min to determine the maximum load applied before failure of the bond between the device and the dura mater. The adhesive strength is defined as the maximum load applied before failure of the bond between the device and the dura mater.

Preferably, the device remains adhesive to the dura mater for a prolonged period of time, sufficient for the dura mater to heal and to close. At the site of the wound, moist conditions are commonly encountered. As such, the device preferably has a durable adhesive strength of more than 1.0 N for at least 24 hours under wet conditions. The durable adhesive strength is determined similarly to the adhesive strength, with the difference that the slices joined by the adhering device are submerged and stored in a saline solution for a certain time period before the breaking point of the bonding of the device with the dura mater is determined. Most preferably, the device has a durable adhesive strength of more than 1.0 N for at least 1 week.

Dura mater typically experiences a pressure of 8-15 mm Hg from the cerobrospinal fluid. Major peak pressures of 70 mmHg, albeit very short, may be experienced due to hiccups, sneezing, coughing and the like. The device in accordance to the present invention therefore preferably has a burst-resistance of at least 8 mmHg, preferably at least 15 mmHg, more preferably at least 30 mmHg, most preferably at least 45 mmHg.

The burst-resistance is determined by closing a container containing a liquid with dura mater. The dura mater is punctured such that a puncture with a diameter of about 3 mm is obtained. The puncture is covered with the device that adheres to the dura mater surrounding the puncture by applying a force of 9.8N for 2 minutes. Then, the pressure in the container is increased such that the liquid contained in the contained exerts a pressure on the device sealing the puncture. The burst-resistance is the point at which leakage occurs.

Preferably, the device remains burst-resistant to the dura mater for a prolonged period of time, sufficient for the dura mater to heal and to close. As such, the device preferably has a durable burst-resistance of at least 8 mmHg, preferably at least 15 mmHg for at least 24 hours. The durability of the burst-resistance is determined similarly to the burst-resistance, with the difference that the punctured dura mater sealed by the device is submerged and stored in a saline solution for a certain time period before the bursting point of the device is determined. Most preferably, the device has a durable burst-resistance of more than 15 mmHg for at least 1 week.

For the purpose of clarity and a concise description features are described herein as part of the same or separate embodiments, however, it will be appreciated that the scope of the invention may include embodiments having combinations of all or some of the features described.

The invention may be illustrated with the following examples.

EXAMPLE 1: PREPARATION OF POLYESTER FOAM DEVICE

A device based on a polymer blend comprising poly(DL-lactide-co-ε-caprolactone) copolymer and tissue-reactive polymer 8-arm NHS-functionalized PEG of 40 kD with a glutarate spacer (8APEGNHS40k) was prepared as follows.

Poly(DL-lactide-co-ε-caprolactone) copolymer (LLC) was prepared by copolymerization of DL-lactide and ε-caprolactone as described in WO2003/066705. 8APEGNHS40k was purchased from Jenkem Technologies.

The copolymer was dissolved in dioxane in a concentration of 2.5 wt % with cyclohexane (2 wt %) as porogen. 8APEGNHS40k was added to yield concentration of 50 mg/mL. The solution was poured in a mold (2×2×1.5 cm) and cooled at −24 C. Freeze-drying of the solidified solutions provided the foam device. In another example molds of 5×5 cm and 10×10 cm were used with the appropriate amount of the solutions.

EXAMPLE 2: PREPARATION OF A MULTILAYERED POLYESTER FOAM DEVICE

A solution is prepared according to Example 1, 1 mL from this solution is poured in a mold (2×2×1.5 cm) and the mold is subsequently cooled (−24° C.) until the solution has solidified. On top of the frozen solution 1 mL of a second solution containing PEG-OH (20 k) in 1,4-dioxane (conc.) is added. The mold is placed at −24° C. until the entire content of the mold has solidified. The mold is placed in the freeze-dryer and the solvent is removed overnight.

EXAMPLE 3: PREPARATION OF A POLYESTER FOAM DEVICE WITH A DENSE SHEET ON ONE SIDE

A solution of polyurethane (about 2 wt %) in chloroform is cast in a mold as described in example 2. After evaporation of the solvent a sheet is obtained. The mold and the sheet are cooled at −24° C.

The LCC copolymer of Example 1 was dissolved in dioxane in a concentration of 2.5 wt % with cyclohexane (2 wt %) as porogen. 8APEGNHS40k was added to yield concentration of 50 mg/mL. The solution was poured on top of the cooled sheet in the mold (2×2×1.5 cm) and subsequently cooled at −24 C. Freeze-drying of the solidified solutions provided the foam device. In other examples molds of 5×5 cm and 10×10 cm were used with the appropriate amount of the solutions.

EXAMPLE 4: PREPARATION OF A POLYESTER FOAM DEVICE WITH A SHEET ON ONE SIDE AND CONTAINING BUFFER SALT

A solution of polyurethane (about 3 wt %) in chloroform was cast in a mold. After evaporation of the solvent a sheet was obtained. The mold and the sheet were cooled at −24° C.

The LCC copolymer of Example 1 was dissolved in dioxane in a concentration of 2.5 wt %. 8APEGNHS40k was added to yield concentration of 40 mg/mL. To this, disodium hydrogen phosphate was added in 3 mg/mL concentration. The obtained solution was poured on top of the cooled sheet in the mold (7×7×1.5 cm) and subsequently cooled at −24 C. Freeze-drying of the solidified solutions provided the foam device.

EXAMPLE 5: PREPARATION OF AMYLOPECTINE FOAM DEVICE

Amylopectine was mixed with water in a ratio of 1:7 by weight. By heating the suspension (95° C.) under vigorous stirring for 60 minutes a gel was obtained. The gel was poured in a mold (2×2×1.5 cm), cooled (−24° C.) and after freeze-drying a foam of amylopectine was obtained.

EXAMPLE 6 AMYLOPECTIN FOAM DEVICE IMPREGNATED WITH 8APEGNHS COVERED WITH COPOLYESTER SHEET

A foam of amylopectin prepared according to example 5 was impregnated with a solution of tissue reactive polymer (8APEGNHS10k) in chloroform. To obtain a loading of 80 mg tissue reactive polymer in the foam. After evaporation of the solvent the foam is covered with a sheet of copolyester poly(DL-lactide-co-ε-caprolactone) copolymer.

The sheet of the poly(DL-lactide-co-ε-caprolactone) copolymer is covered with a 2 wt % solution of the copolymer in chloroform and the amylopectine foam with tissue reactive polymer is pressed on the sheet. After evaporation of the solvent a foam with a dense sheet on top is obtained.

EXAMPLE 7: DETERMINATION OF ADHESIVE STRENGTH

The adhesive strength of is determined by slicing a piece of porcine dura mater into two slices and adhering the device to both slices such that the slices are joined at their point of slicing. Adherence is achieved by applying a force of 9.8 N for 2 minutes.

By using a universal testing machine, the joined slices are pulled apart at 10 mm/min to determined the force required to break the bonding of the device with the dura mater. The adhesive strength is defined as the maximum load before failure of the bond between the device and the dura mater.

COMPARATIVE EXAMPLE 1: DETERMINATION OF ADHESIVE STRENGTH OF COMMERCIALLY AVAILABLE SEALANTS

In a comparative example, the adhesive strength of commercially available sealants are determined as described in example 7. The results are provided in Table 1.

TissuePatchDural™ is commercially available from Tissuemed, Hemopatch™ and TachoSil™ are commercially available from Baxter.

TABLE 1

| Device | Adhesive strength (N) |
| --- | --- |
| Example 1 (LCC + 8APEGNHS40k) | 1.373 |
| Example 2 multilayered device | 1.560 |
| Example 4 (LCC/8APEGNHS40k/Na$_2$HPO$_4$ buffer) + copolyurethane sheet | 6.9 |
| Example 5 amylopectin device | 0.13 |
| Example 6 (amylopectin/8APEGNHS10k) + copolyester sheet | |
| Comparative examples | |
| TissuePatchDural ™ | 0.439 |
| Hemopatch ™ | 0.487 |
| Tachosil ™ | 0.850 |

EXAMPLE 8: DETERMINATION OF DURABLE ADHESIVE STRENGTH

Devices given in table 2 were prepared comparable to example 1, but with tissue-reactive polymers with a different number of arm and a different molecular weight.

The durable adhesive strengths of the devices were tested in a method comparable to example 7, with the difference that the slices joined by the adhering device are submerged and stored in a saline solution for a certain time period (0-168 h, as indicated in table 2) before the adhesive strength of the device with the dura mater is determined. The results are given in table 2.

TABLE 2

| Time (h) | Devices | | | Comp. device Tachosil |
|---|---|---|---|---|
| | LCC + 8APEGNHS40k | LCC + 4APEGNHS10k | LCC + 8APEGNHS10k | |
| 0 | 1.37 | 0.98 | 0.7 | 0.85 |
| 24 | 2.44 | | | 0 |
| 96 | 2.17 | 1.71 | 1.02 | 0 |
| 168 | 1.61 | 1.74 | 1.46 | 0 |

EXAMPLE 9: DETERMINATION OF ADHESIVE STRENGTH DEPENDENT IN PEG MULTI-ARM BASED DEVICES

Three different devices (devices #1-3), each comprising the same concentration of a different tissue-adhesive polymer having a NHS-comprising PEG arms were provided as described in Example 1.

The adhesive strength of each device on dura mater was determined as described in Example 7.

Device #1-1 arm: 1PEGNHS2k (1 mmol NHS per gram polymer)

Device #2-4 arms: 4PEGNHS10k (0.4 mmol NHS per gram polymer)

Device #3-8 arms: 8PEGNHS40k (0.2 mmol NHS per gram polymer)

Figure 3:
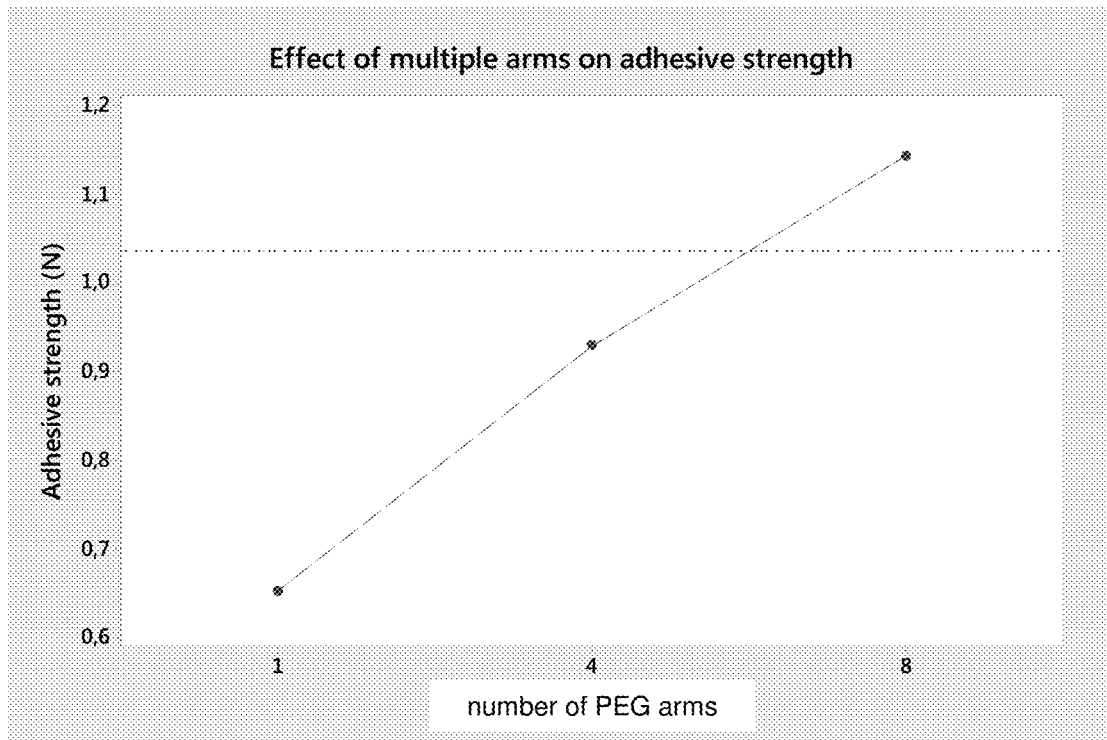
FIG. 3 graphically depicts the effect of multiple PEG arms on adhesive strength.

The adhesive strength is provided in FIG. 3. The results show that, despite less NHS per gram of polymer, multi-arm PEG tissue-adhesive polymer devices demonstrate a relatively high adhesive strength to dura mater.

EXAMPLE 10: BURST-RESISTANCE

The burst-resistance of devices obtained from examples 1 and 2 were determined by closing a container containing a liquid with dura mater. The dura mater is punctured such that a puncture with a 3 mm diameter is obtained. The puncture is covered with the device that adheres to the dura matter surrounding the puncture by applying a force of 9.8 N for 2 minutes. Then, the pressure in the container is increased such that the liquid contained in the contained exerts a pressure on the device sealing the puncture. The burst-resistance is the point at which the device bursts.

Results are provided in table 3.

COMPARATIVE EXAMPLE 2: BURST-RESISTANCE OF COMMERCIALLY AVAILABLE SEALANTS

In a comparative example, the burst-resistance of commercially available sealants are determined as described in example 10. The results are provided in Table 3.

TABLE 3

| Device | burst-resistance(mmHg) |
|---|---|
| Example 1 LCC + 8APEGNHS40k | 59 |
| Example 1 LCC + 8APEGNHS40k (after 24 h in saline) | 16 |
| Example 4 (LCC + 8APEGNHS40k + Na$_2$HPO$_4$ buffer) + copolyester sheet | 106 |
| Example 5 Amylopectine | 14 |
| Example 6 (amylopectin/ 8APEGNHS10k) + copolyester sheet | 51 |
| Comparative devices | |
| Hemopatch ™ | 19 |
| TissuePatchDural ™ | 7 |

EXAMPLE 11: EFFECT OF BUFFER ON DEGRADATION OF POLY(DL-LACTIDE-CO-ε-CAPROLACTONE) COPOLYMER (LLC)

The poly(DL-lactide-co-ε-caprolactone) copolymer (LLC) as prepared in Example 1 was dissolved in dioxane in a concentration of 2.5 wt and one of three different buffer solutions (phosphate, bicine, carbonate) was added in 3 mg/mL concentration. The obtained solution cooled at −24 C and freeze-dried to provided the foam device.

The foam device was placed in a physiological solution at 40° C., 80% relative humidity and the degradation of the LLC copolymer was monitored in time.

Figure 4:
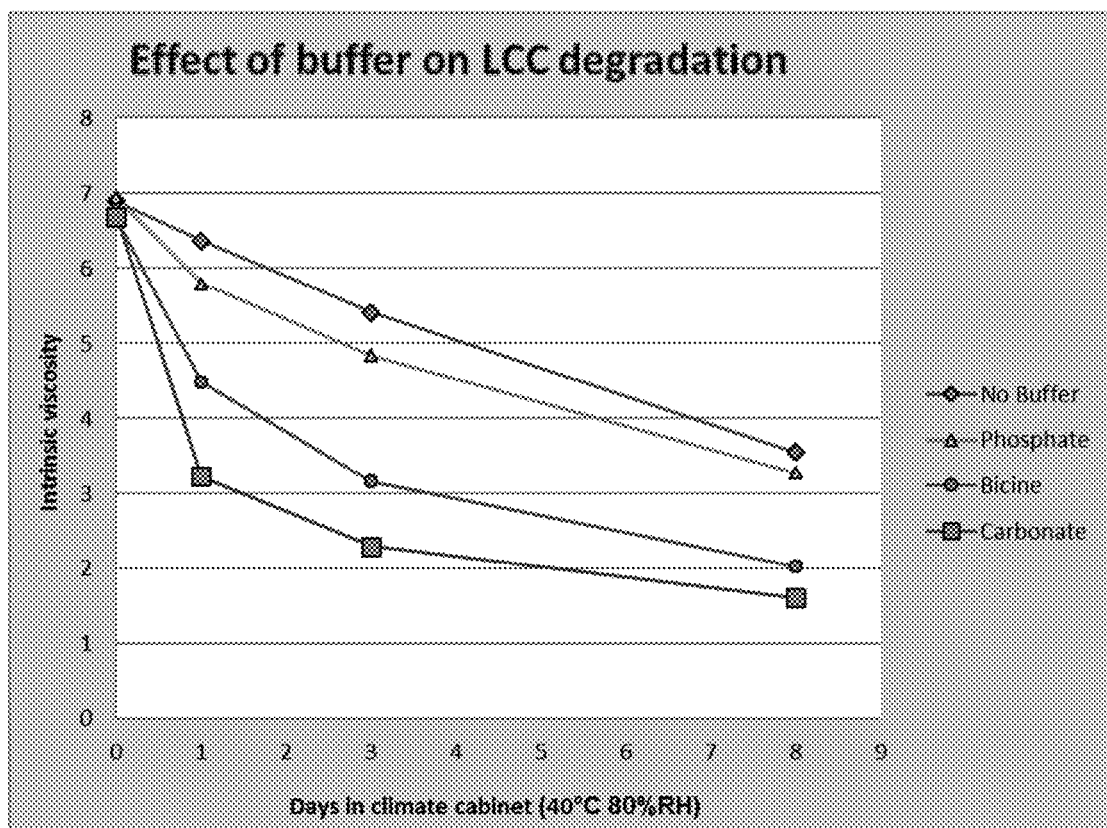
FIG. 4 graphically depicts the effect of buffer on LCC degradation.

The results are provided in FIG. 4. The presence of the buffer in the foam does not have a detrimental negative effect on the degradation of the foam.

The invention claimed is:

1. A tissue-adhesive device for sealing dura mater comprising a multilayered structure having at least a first layer and a second layer,
   the first layer comprising a foam structure including a tissue-adhesive polymer blend comprising a bioresorbable carrier polymer and a bioresorbable synthetic tissue-reactive polymer, wherein the synthetic tissue-reactive polymer comprises a multi-arm polyethylene glycol functionalized with at least one tissue-reactive group that comprises an activated ester, and
   the second layer comprising a sheet structure, wherein the sheet structure includes a polyurethane.

2. The tissue-adhesive device of claim 1, having an adhesive strength of more than 1 N.

3. The tissue-adhesive device of claim 1, having a burst-resistance of at least 8 mmHg.

4. The tissue-adhesive device of claim 1, having a burst-resistance of at least 15 mmHg.

5. The tissue-adhesive device of claim 1, having a burst-resistance of at least 30 mmHg.

6. The tissue-adhesive device of claim 1, having a burst-resistance of at least 45 mmHg.

7. The tissue-adhesive device of claim 1, wherein the carrier polymer is a synthetic carrier polymer and comprises one or more of a polyester, polyether, polyhydroxyacid, polylactone, polyetherester, polycarbonate, polydioxane, polyanhydride, polyurethane, polyester(ether)urethane, polyurethane urea, polyamide, polyesteramide, poly-orthoester, polyaminoacid, polyphosphonate, and polyphosphazene.

8. The tissue-adhesive device of claim 7, wherein the synthetic carrier polymer comprises a poly(DL-lactide-co-ε-caprolactone) copolymer.

9. The tissue-adhesive device of claim 1, wherein the carrier polymer is a biological polymer comprising a polysaccharide.

10. The tissue-adhesive device of claim 1, wherein the activated ester is selected from the group consisting of a thioester, a perfluoroalkyl ester, pentafluorophenol ester, and N-hydroxysuccinimide ester and derivatives thereof.

11. The tissue-adhesive device of claim 1, wherein the tissue-reactive polymer comprises a 4-arm or an 8-arm polyethylene glycol.

12. The tissue-adhesive device of claim 1, wherein the tissue-reactive polymer has a molecular weight of up to 100000 g/mol.

13. The tissue-adhesive device of claim 1, wherein the weight ratio of the carrier polymer to the tissue-reactive polymer in the material is 1:10 to 10:1.

14. The tissue-adhesive device of claim 1, wherein the tissue-adhesive polymer blend further comprises a filler polymer comprising polyethylene glycol that is not functionalized with the tissue-reactive functional group.

15. The tissue-adhesive device of claim 1, wherein the tissue-adhesive polymer blend further comprises a buffering agent selected from the group consisting of a phosphate, carbonate, acetate, citrate, Good's buffers and combinations thereof.

16. The tissue-adhesive device of claim 1, wherein the tissue-reactive polymer has a number-averaged molecular weight of 20000 g/mol or more.

17. The tissue-adhesive device of claim 1, wherein the tissue-reactive polymer has a number-averaged molecular weight of 20000 to 80000 g/mol.

18. The tissue-adhesive device of claim 1, wherein the polyurethane is a polyester polyurethane copolymer obtained by polymerizing diisocyanate linked polyester polymer and diol components.

19. The tissue-adhesive device of claim 18, wherein the polyester polyurethane copolymer is obtained by polymerizing a 50/50 mol % poly(DL-lactide-co-ε-caprolactone) prepolymer (PP) end-capped with 1,4-diisocyanatobutane with a diol having the structure HO(CH$_2$)$_4$—OC(O)NH—(CH$_2$)$_4$—NHC(O)O—(CH$_2$)$_4$OH.

* * * * *